United States Patent [19]

Zelmanovic et al.

[11] Patent Number: 4,631,408

[45] Date of Patent: Dec. 23, 1986

[54] METHOD OF SIMULTANEOUSLY DETERMINING GAUGE AND ORIENTATION OF POLYMER FILMS

[75] Inventors: David Zelmanovic, Monsey; Stanley J. Kishner, Pomona, both of N.Y.

[73] Assignee: Kollmorgen Technologies Corporation, Dallas, Tex.

[21] Appl. No.: 653,962

[22] Filed: Sep. 24, 1984

[51] Int. Cl.[4] ............................................. G01J 1/00
[52] U.S. Cl. .................. 250/339; 250/340; 250/341
[58] Field of Search .................. 250/339, 358.1, 341, 250/340; 356/381, 382, 432, 442

[56] References Cited

U.S. PATENT DOCUMENTS

| | | | |
|---|---|---|---|
| 3,448,268 | 6/1969 | Proctor | 250/341 |
| 3,631,526 | 11/1969 | Brunton | 250/341 |
| 3,825,755 | 7/1974 | Ruskin | 250/339 |
| 4,027,161 | 5/1977 | Williams et al. | 250/339 |
| 4,243,882 | 1/1981 | Yasujima et al. | 250/341 |
| 4,429,225 | 1/1984 | Fumoto et al. | 250/339 |
| 4,490,612 | 12/1984 | Törmälä | 250/341 |
| 4,521,111 | 6/1985 | Paulsen et al. | 250/461.1 |

FOREIGN PATENT DOCUMENTS

| | | | |
|---|---|---|---|
| 822394 | 9/1969 | Canada | 250/339 |
| 2127541 | 9/1983 | United Kingdom | 250/339 |

OTHER PUBLICATIONS

Wolfram et al, "An Improved IR Method for Meas. Struct. and Orientation in Polymers Applied Spectroscopy", vol. 24, #2, p. 263 (1970).

Primary Examiner—Carolyn E. Fields
Assistant Examiner—Richard Hanig
Attorney, Agent, or Firm—Morgan & Finnegan

[57] ABSTRACT

In the manufacture of a multilayer polymer film, the thickness and degree of orientation are simultaneously measured. A beam of infrared radiation having predetermined wavelengths is either transmitted through or reflected by the polymer film to be measured and received by a photodetector. The photodetector provides an electrical output signal which can be analyzed to determine the thickness and degree of orientation.

28 Claims, 7 Drawing Figures

A.
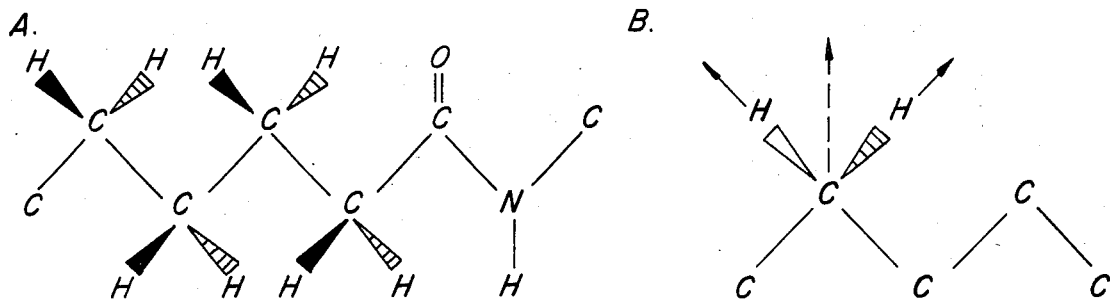
PORTION OF NYLON 66 REPEAT UNIT SHOWING ZIG ZAG ARRANGEMENT IN PLANE OF PAPER AND PARALLEL TO MACHINE DIRECTION.

B.

C-H STRETCH

C.
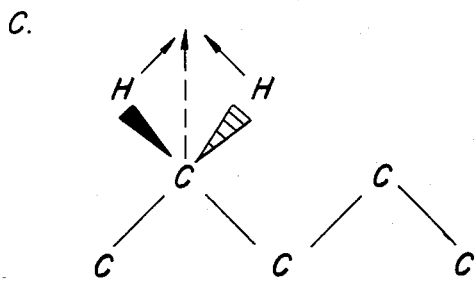
H-C-H BEND

D.
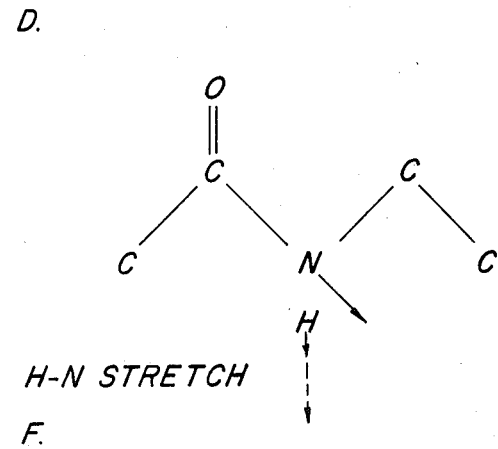
H-N STRETCH

E.
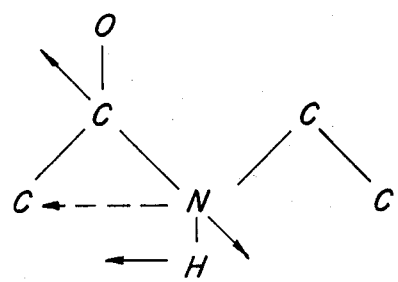
CONH VIBRATION

F.
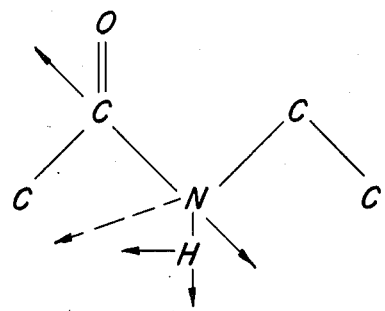
COMBINATION OF D & E

Y (TRANSVERSE DIRECTION)
Z (DIRECTION PERPENDICULAR TO PLANE OF PAPER)
X (MACHINE DIRECTION)

SOLID WEDGE (▬▬): OUT OF PLANE OF PAPER TOWARD VIEWER
DASHED WEDGE (▭▭▷): OUT OF PLANE OF PAPER AWAY FROM VIEWER
──▶ INDICATES DIRECTION OF NUCLEAR MOTION
── ─▶ INDICATES DIRECTION OF RESULTANT $d_\mu$

FIGURE 1

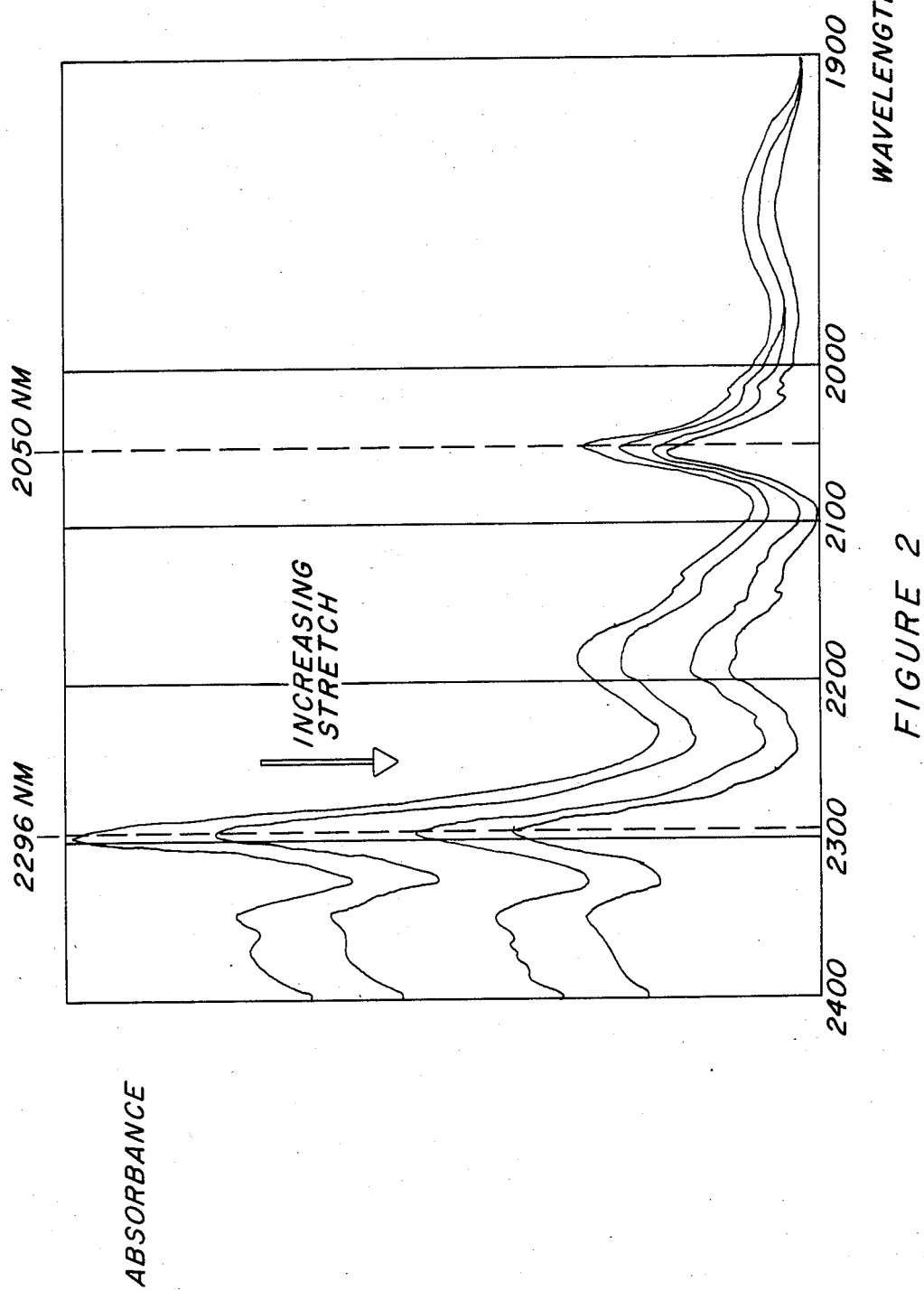

METHOD OF SIMULTANEOUSLY DETERMINING GAUGE AND ORIENTATION OF POLYMER FILMS

BACKGROUND OF THE INVENTION

1. Field of the Invention

The present invention relates generally to the measurement of films and more specifically to the simultaneous determination of the gauge and orientation of polymer films.

2. Description of the Prior Art

The present trend in the production of flexible packaging is toward multilayer polymer structures that contain a number of materials. The reason is that, quite often, no single material has the combination of physical and chemical properties required for the application. Furthermore, there is a trend away from the use of foil and paper, both of which require large amounts of energy to manufacture, and are consequently expensive. Polymer films are being used in their place.

Multilayer structures utilizing polymer films can be produced by lamination, coating or coextrusion processes. In coextrusion, a number of films are simultaneously extruded through a common die. This coextrusion process allows very thin layers of high performance, expensive polymers to be coextruded along with less expensive materials, to produce low cost, yet high performance, flexible packaging materials.

Coextrusions are used to make trash bags, meat wraps, shipping sacks, cheese and snack packaging, cereal liners and bakery overwrap, among other things. As an example, polyethelene (PE) and nylon are often used in combination in snack food bags, because nylon has good strength and toughness and is a good oxygen and carbon dioxide barrier, while PE is a good moisture barrier. In addition, PE carries printing ink and other coatings well.

In the manufacture of any multilayer polymer film, the thickness or gauge of the individual layers as well as the total thickness will vary as a function of process parameters. Thus, in order to manufacture a multilayer structure with adequate thickness in each layer, the average layer thickness will be made to exceed the minimum required so that thickness variations do not result in regions of inadequate thickness. If, however, thickness could be controlled, then less polymer would be required, on average. In lamination applications, individual layers exist prior to being integrated into the final multilayer structure, and therefore may be gauged independently by appropriate methods. In coating applications, layers are added one at a time, and may therefore be gauged by measuring the increased thickness of the product after each coating operation. However, this is not the case in coextruded structures. The polymer films are combined in the coextrusion die, and do not exist individually. Therefore, it is necessary to gauge the different materials simultaneously, in the presence of one another. It is desirable that such gauging be conducted on-line to minimize down time and reduce on-line waste. On-line gauging also facilitates closed-loop control of the process. It is also desirable that such gauging require little or no calibration by an operator because of time waste and the subjective nature of most operator intervention. In the same regard, it is desirable to gauge the thickness of a particular coextrusion under various conditions of overall gauge and relative composition without recalibration. The gauging method should be nondestructive and non-contact, of course.

There are three common on-line gauging methods: caliper, nuclear and infrared (IR). Caliper gauges are of contact and non-contact types. The majority of caliper gauges operate on the principles of magnetic reluctance or inductance. These methods are insensitive to compositional variations in the coextrusion, and, therefore, are unable to distinguish individual materials in a co-extrusion.

Nuclear gauges are non-contact. They operate by passing radiation (usually $\beta$ particles) through the film being gauged. Again, they are relatively insensitive to compositional variations, and are capable of measuring only total gauge. They are not appropriate for co-extrusions.

IR gauges (here inclusive of radiation of wavelength 1–50 microns) are non-contact. They operate by passing IR radiation through the sample. In contrast to the other methods, the IR technique can distinguish individual materials, since the transmission of IR radiation of given wavelength is a function of the material through which it passes. In general, the infrared transmittance of a film is given by $$T(\lambda) = e^{-\alpha(\lambda)d} \quad (1)$$

where d is the film thickness, $\alpha(\lambda)$ is the absorption coefficient, and $\lambda$ is the wavelength of the infrared radiation. This simple relationship is known as Beer's Law. (See, for example, G. Barrow, "Introduction to Molecular Spectroscopy", McGraw Hill, N.Y. 1962). A more common mathematical form is found by taking logarithms of equation (1) to get $$A(\lambda) = \alpha(\lambda)d \quad (2)$$

where $A(\lambda)$ is the absorbance, or the negative logarithm of transmittance $T(\lambda)$. For multilayer films, e.g. coextrusions, Beer's Law can be applied n times for n materials if the absorption bands do not overlap in the n materials. Such a situation rarely exists in practice. A more sophisticated and realistic approach accounts for spectral overlap by solving simultaneously for the absorptions of each of n materials at the n wavelengths. This multivariate form of Beer's Law is given by:

$$A(\lambda_1) = \alpha_1(\lambda_1)d_1 + \alpha_2(\lambda_1)d_2 + \ldots + \alpha_n(\lambda_1)d_n \quad (3)$$
$$A(\lambda_2) = \alpha_1(\lambda_2)d_1 + \alpha_2(\lambda_2)d_2 + \ldots + \alpha_n(\lambda_2)d_n$$
$$\cdot$$
$$\cdot$$
$$\cdot$$
$$A(\lambda_n) = \alpha_1(\lambda_n)d_1 + \alpha_2(\lambda_n)d_2 + \ldots + \alpha_n(\lambda_n)d_n$$

Here, n is the number of materials, $\lambda_i$ is the wavelength chosen that is most sensitive to changes in thickness of the $i^{th}$ material, $\alpha_i(\lambda_j)$ is the absorption coefficient of the $i^{th}$ material at the $j^{th}$ wavelength, and $d_i$ is the thickness of the $i^{th}$ material. In equation (3), the absorbances $A(\lambda_i)$ are measured and the absorption coefficients $\alpha_i(\lambda_j)$ are known. The equations are then solved for the thicknesses $d_i$. It should be noted that often the absorbance $A(\lambda_i)$ is replaced by an absorbance difference $\alpha(\lambda_i) - A(\lambda_i')$ in order to account for baseline variations.

The absorption of IR radiation by polymer molecules results from the interaction between changing dipole moments in the material and the electric vector of incident radiation. In fact, the absorption coefficient is proportional to the square of the dot product of the change in dipole moment $\vec{d\mu}$ and the electric vector E of the electromagnetic radiation. This dot product is given by $$\vec{d\mu}\cdot\vec{E}=(d\mu)(E)\cos\phi, \qquad (4)$$

where $\phi$ is the angle between them. In an isotropic medium, the absorption coefficient $\alpha_i(\lambda_j)$ is independent of the direction of propagation of the radiation. In the case of anisotropic media, however, $\alpha_i(\lambda_j)$ is more properly designated as $\alpha_i^k(\lambda_j)_{k=x,y,z}$ where x, y and z are the measurement axis directions. Additionally $\alpha_i(\lambda_j)$ can change if the orientation of the medium is changed as a result of applied stresses. This orientation results in alignment of the long macromolecular chains that comprise the polymer film. The chains tend to line up in the direction of applied stress. Groups that are part of the chain backbone and pendant on the backbone will move along with the chain without serious deformation, at least to a first approximation. Thus, the position, relative to the measurement axis system, of the dipoles responsible for the vibrational transitions that give rise to absorption of infrared light will change. The interaction between these changing dipoles and the electric vector of incident radiation will, of course, also change and thus the absorption coefficient will change.

It is well known that the blown-film extrusion process imparts stresses to the film. Starting in the die, the molten plastic undergoes shear forces upon extrusion through the die lips. Upon being blown into a tube, the film walls have a force applied to them in a direction transverse to the direction of motion of the film. The magnitude of this force determines the diameter of the tube and hence the width of the film web. Additionally, the film experiences a force in the longitudinal or machine direction, exerted by the take up rollers. The film is stretched in the machine direction, thereby determining its gauge. Finally, the tube is slit or collapsed to form a web. These transverse and longitudinal stresses induce strain in the layers comprising the coextrusion. The stresses result in orientation of the long chain macromolecules. It is also important to note that the coextrusion is under stress even after being cut from the roll. Each layer is in intimate contact with two other layers, except for the outer layers which are contacted on one side only. These sandwich layers serve to keep the inner layer rigid. More importantly, the stress and corresponding strain are not fixed when the film is cut from the roll. The coextruded film undergoes stress relaxation and this relaxation changes the orientation of the macromolecules in each layer of the film. The film does not simply mechanically recover from the stress since stress is still being applied, as indicated above. Consequently, absorbances at the chosen wavelengths will change in time. Also, physical properties such as material strength and chemical properties such as permeability to gases such as oxygen, carbon dioxide and nitrogen, and liquids such as water, are related orientation. As the film relaxes, these properties change. It is therefore important that the manufacturer examine the product before shipment.

The fact that polymer films are oriented complicates the on-line gauging of such films. The infrared gauging technique requires knowledge of the absorption coefficient at each wavelength. Since the absorption coefficient varies with orientation, the standard infrared gauging techniques as expressed in equations (2) and (3), become inadequate because they incorrectly assume the constancy of $\alpha_i(\lambda_j)$. It is also important to note that since orientation of polymer films affects their physical and chemical properties, it is also useful to be able to measure degree of orientation by an on-line, non-contact method.

There are a number of infrared techniques that have been used for measuring the gauge of polymer films. The simplest technique involves the measurement of the infrared absorption at a single wavelength (or wavelength pair), and calculation of thickness according to Beer's Law. Williams and Pugh (U.S. Pat. No. 4,027,161) describe a method of minimizing interference effects in such an instrument. Fumoto and Sawaguchi describe another solution to this problem (U.S. Pat. No. 4,429,225). A means of modulating the photodetectors in a infrared film gauging system is described by Ruskin (U.S. Pat. No. 3,825,755). An infrared sensor designed to measure coextruded films is described by B. Burk, in an article entitled "Infrared Sensors Control Thickness of Film-Coextrusion Plies," Modern Plastics, January 1984, pp. 84–8. This technique utilizes multiple wavelengths, but relies on non-overlap of absorption bands. This is a very restrictive technique, only applicable to a few special cases. Furthermore, it does not account for absorption coefficient changes resulting from orientation. The use of multiwavelength measurements with overlapping absorption bands is described in an articles entitled "New Sensors Tackle The Tough Jobs: Coextrusions, Foam, Filled Material", Modern Plastics, September 1979, pp. 88–91. Simultaneous equations are used in a multivariate analysis to measure the gauges of different polymers in a coextrusion. This technique does not account for orientation. The use of the multivariate approach in near IR instrumentation is described by R. Rosenthal, in "An Introduction to Near Infrared Quantitative Analysis," presented at the 1977 Annual Meeting of the American Association of Cereal Chemists. Reference is made to the measurement of the thickness of the layers in coextruded films. This technique, as stated previously, does not account for polymer orientation.

Two well-known techniques used to determine polymer orientation are dichroism and birefringence. The dichroic ratio is defined as the ratio of absorption of light polarized in a given direction to that polarized in the perpendicular direction (H. W. Siesler and K. Holland-Moritz, "Infrared and Raman Spectroscopy of Polymers," Marcell Decker, Inc. N.Y. (1980) p. 229). Dichroism requires anisotropy of absorption which in the IR region requires anisotropy of $\vec{d\mu}$ for vibrational motion. Dichroism measurements on polymer films (Zbinden, "Infrared Spectroscopy Of High Polymers" Academic Press, N.Y. (1964), p. 212) are extremely useful for the determination of molecular orientation in polymers. However, the dichroic ratio, which is independent of thickness, cannot simultaneously determine orientation and film gauge.

Birefringence is defined as the difference between the refractive indices of a material as measured in two mutually perpendicular directions (Shurcliff "Polarized Light," Harvard University Press (1962), Chapter 7). Birefringence is associated with the anisotropy of the polarizability of the molecules comprising the material. Birefringence can be determined by placing the material between two polarizers whose major transmission axis are mutually perpendicular (crossed) and measuring the intensity of light that exits the crossed polarizers. If the material is not birefringent, no light exits the second polarizer. If it is, it renders the incident linearly polarized light elliptical by retarding the phase of one component of light relative to the other. This introduces a component of light perpendicular to that incident on the material. This perpendicular component exits the second polarizer. Birefringence measurements are used extensively to determine molecular orientation in polymer films (R. J. Samuels, "Structured Polymer Properties," John Wiley and Sons, N.Y. (1974) pp. 41–74). Since the birefringence is measured by using phase retardation, and phase retardation is proportional to thickness as well as birefringence, birefringence measurements themselves require independent means of determining sample thickness. Obviously, then, birefringence measurements alone cannot be used to determine film gauge.

It is therefore an object of this invention to provide a method of measuring the gauge of polymer films with infrared radiation, independent of the degree of orientation of the films. It is a further object of this invention to measure, simultaneously, the thickness of multiple polymer materials in a laminated, coated or coextruded structure, independent of the degree of orientation of each of the materials.

It is a further object of this invention to measure simultaneously, both the thickness and degree of orientation of polymer films.

It is a still further object of this invention to measure the degree of orientation of polymer films, independent of their thicknesses.

It is a still further object of this invention to measure, simultaneously, the thicknesses and degrees of orientation of polymer films, without the need for experimentally determining, for each production run, the value of the absorption coefficients.

It is a still further object of this invention to provide an on-line, non-contact method of measuring both the thickness and degree of orientation of polymer films.

SUMMARY OF THE INVENTION

The present invention provides methods and devices for simultaneously measuring the thickness and degree of orientation of multilayer polymer films. The output of a light source is filtered by a rotating plurality of filters to provide infrared radiation having predetermined wavelengths. The infrared radiation measurement beam is either transmitted through or reflected by the polymer film and received by a photodetector. The beam of infrared radiation may also be split prior to irradiating the polymer film in order to provide a reference beam which increases the sensitivity of the measurement. The beams are directed onto a photodetector which converts them to electrical output signals. The electrical output signals are preferably processed by a suitably programmed computer to provide an indication of the thickness of the polymer film and its degree of orientation.

BRIEF SUMMARY OF THE DRAWINGS

FIG. 1 shows a structural representation of the nylon 6,6 molecule, and depicts the various vibrational modes responsible for infrared absorbances.

FIG. 2 shows graphs of the absorption spectra for four different degrees of orientation of nylon 6.6.

DETAILED DESCRIPTION OF THE INVENTION

Figure 3:
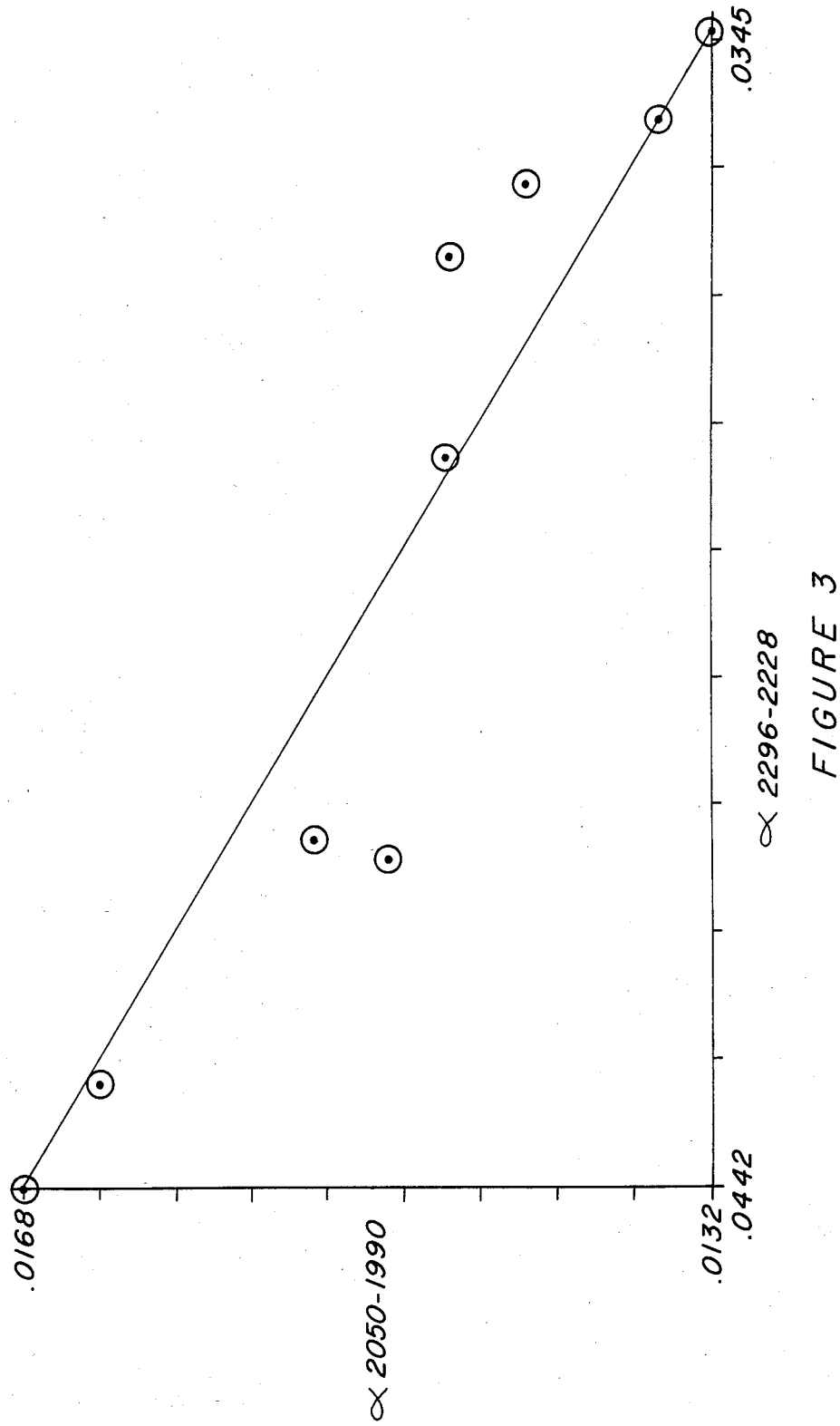
FIG. 3 shows a graph of the nylon absorption coefficient at 2050 nm. vs. the nylon absorption coefficient at 2296 nm.

When multiple materials are present in a coextruded structure, the standard multivariate analysis, as given mathematically in equation (3), is used. As previously described, however, changes in orientation of the polymer materials cause absorption coefficients to change. Since the absorption coefficient is now an additional unknown for each material, it is necessary to measure absorbance at an additional wavelength for each material. This will give us 2n equations with which to solve for 2n unknowns—n thicknesses and n absorption coefficients. The equations take the following form:

$$A(\lambda_{1a}) = \alpha_1(\lambda_{1a})d_1 + \alpha_2(\lambda_{1a})d_2 + \ldots \alpha_n(\lambda_{1a})d_n \quad (5)$$

$$A(\lambda_{1b}) = \alpha_1(\lambda_{1b})d_1 + \alpha_2(\lambda_{1b})d_2 + \ldots \alpha_n(\lambda_{1b})d_n$$

$$A(\lambda_{2a}) = \alpha_1(\lambda_{2a})d_1 + \alpha_2(\lambda_{2a})d_2 + \ldots \alpha_n(\lambda_{2a})d_n$$

$$A(\lambda_{2b}) = \alpha_1(\lambda_{2b})d_1 + \alpha_2(\lambda_{2b})d_2 + \ldots \alpha_n(\lambda_{2b})d_n$$

.
.
.

$$A(\lambda_{na}) = \alpha_1(\lambda_{na})d_1 + \alpha_2(\lambda_{na})d_2 + \ldots \alpha_n(\lambda_{na})d_n$$

$$A(\lambda_{nb}) = \alpha_1(\lambda_{nb})d_1 + \alpha_2(\lambda_{nb})d_2 + \ldots \alpha_n(\lambda_{nb})d_n$$

The wavelenth subscripts "na" and "nb" designate the two wavelengths chosen for the $n^{th}$ material. The choice of these two wavelengths will be discussed below. It should also be remembered that each absorbance is often replaced with an absorbance difference, usually at two closely spaced wavelengths. The choice of these wavelength pairs will also be described below.

The system of 2n equations (5) has n unknown thicknesses $d_i$. Although there are $2n^2$ absorption coefficients, there are only n independent coefficients, since all absorptions coefficients for any one material can be expressed as a function of the absorption coefficient at an arbitrary wavelength. That is, all of the $\alpha_1$'s can be expressed as functions of $\alpha_1(\lambda_{1a})$ all of the $\alpha_2$'s can be expressed as functions of $\alpha_2(\lambda_{2a})$, and, in general, all of the $\alpha_n$'s can be expressed as functions as $\alpha_n(\lambda_{na})$. To do this, it is necessary to empirically determine the effect of stress on the various absorption coefficients. Having done so, the system of equations (5) can be rewritten as follows:

$$A(\lambda_{1a}) = \alpha_1 d_1 + g_1(\alpha_2)d_2 + \ldots + h_1(\alpha_n)d_n \quad (6)$$

$$A(\lambda_{1b}) = f_1(\alpha_1)d_1 + g_2(\alpha_2)d_2 + \ldots + h_2(\alpha_n)d_n$$

-continued
$$A(\lambda_{2a}) = f_2(\alpha_1)d_1 + a_2d_2 + \ldots + h_3(\alpha_n)d_n$$

$$A(\lambda_{2b}) = f_3(\alpha_1)d_1 + g_3(\alpha_2)d_2 + \ldots + h_4(\alpha_n)d_n$$

$$\vdots$$

$$A(\lambda_{na}) = f_{2n-2}(\alpha_1)d_1 + g_{2n-2}(\alpha_2)d_2 + \ldots + \alpha_n d_n$$

$$A(\lambda_{nb}) = f_{2n-1}(\alpha_1)d_1 + g_{2n-1}(\alpha_2)d_2 + \ldots + h_{2n-1}(\alpha_n)d_n$$

Note that we have simplified the notation, where $\alpha_1$, $\alpha_2$, ... $\alpha_n$ are the independent absorption coefficients. All of the functional forms (f, g, ..., h) are determined experimentally. The set of 2n simultaneous equations is nonlinear in $\alpha_i$ and d since these variables appear as a product. Solutions can be obtained by using the Newton-Raphson method generalized for solution of simultaneous nonlinear equations. (See for example, D. McCracken and W. Dorn, "Numerical Methods and Fortran Programming", J. Wiley & Sons, N.Y. 1964).

The general form of the Newton-Raphson solution for a set of simultaneous non-linear equations follows. Referring to the set of equations (6), designate the right side of each equation simply as $X_{ia}$ or $X_{ib}$. The Newton Raphson equations are then;

$$A(\lambda_{1a}) - X_{1a} = \frac{\partial X_{1a}}{\partial \alpha_1}\Delta\alpha_1 + \frac{\partial X_{1a}}{\partial d_1}\Delta d_1 + \frac{\partial X_{1a}}{\partial \alpha_2}\Delta\alpha_2 + \quad (7)$$

$$\frac{\partial X_{1a}}{\partial d_2}\Delta d_2 + \ldots + \frac{\partial X_{1a}}{\partial \alpha_n}\Delta\alpha_n + \frac{\partial X_{1a}}{\partial d_n}\Delta d_n$$

$$A(\lambda_{1b}) - X_{1b} = \frac{\partial X_{1b}}{\partial \alpha_1}\Delta\alpha_1 + \frac{\partial X_{1b}}{\partial d_1}\Delta d_1 + \frac{\partial X_{1b}}{\partial \alpha_2}\Delta\alpha_2 +$$

$$\frac{\partial X_{1b}}{\partial d_2}\Delta d_2 + \ldots + \frac{\partial X_{1b}}{\partial \alpha_n}\Delta\alpha_n + \frac{\partial X_{1b}}{\partial d_n}\Delta d_n$$

$$A(\lambda_{2a}) - X_{2a} = \frac{\partial X_{2a}}{\partial \alpha_1}\Delta\alpha_1 + \frac{\partial X_{2a}}{\partial d_1}\Delta d_1 + \frac{\partial X_{2a}}{\partial \alpha_2}\Delta\alpha_2 +$$

$$\frac{\partial X_{2a}}{\partial d_2}\Delta d_2 + \ldots + \frac{\partial X_{2a}}{\partial \alpha_n}\Delta\alpha_n + \frac{\partial X_{2a}}{\partial d_n}\Delta d_n$$

$$A(\lambda_{2b}) - X_{2b} = \frac{\partial X_{2b}}{\partial \alpha_1}\Delta\alpha_1 + \frac{\partial X_{2b}}{\partial d_1}\Delta d_1 + \frac{\partial X_{2b}}{\partial \alpha_2}\Delta\alpha_2 +$$

$$\frac{\partial X_{2b}}{\partial d_2}\Delta d_2 + \ldots + \frac{\partial X_{2b}}{\partial \alpha_n}\Delta\alpha_n + \frac{\partial X_{2b}}{\partial d_n}\Delta d_n$$

$$\vdots$$

$$A(\lambda_{na}) - X_{na} = \frac{\partial X_{na}}{\partial \alpha_1}\Delta\alpha_1 + \frac{\partial X_{na}}{\partial d_1}\Delta d_1 + \frac{\partial X_{na}}{\partial \alpha_2}\Delta\alpha_2 +$$

$$\frac{\partial X_{na}}{\partial d_2}\Delta d_2 + \ldots + \frac{\partial X_{na}}{\partial \alpha_n}\Delta\alpha_n + \frac{\partial X_{na}}{\partial d_n}\Delta d_n$$

$$A(\lambda_{nb}) - X_{nb} = \frac{\partial X_{nb}}{\partial \alpha_1}\Delta\alpha_1 + \frac{\partial X_{nb}}{\partial d_1}\Delta d_1 + \frac{\partial X_{nb}}{\partial \alpha_2}\Delta\alpha_2 +$$

$$\frac{\partial X_{nb}}{\partial d_2}\Delta d_2 + \ldots + \frac{\partial X_{nb}}{\partial \alpha_n}\Delta\alpha_n + \frac{\partial X_{nb}}{\partial d_n}\Delta d_n$$

where $\Delta\alpha_i = \alpha_{i,Q} - \alpha_{i,Q-1}$ and $\Delta d_i = d_{i,Q} - d_{i,Q-1}$ and Q is the Qth approximation to the value of $\alpha_i$ and $d_i$. An initial guess is made for the correct values of $\alpha_1$ and $d_1$. These are $\alpha_{i,o}$ and $d_{i,o}$. The $\alpha_{i,1}$ and $d_{i,1}$ are determined straightforwardly because the 2n Newton-Raphson equations are linear in the 2n unknowns $\alpha_i$, $d_i$, i=1 to n. Then, $\alpha_{i,1}$ and $d_{i,1}$, become the new $\alpha_i$, Q−1 and $d_i$, Q−1, and the process is repeated until $\Delta\alpha_i$ and $\Delta d_i$ are all satisfactorily small, indicating that a solution is being approached.

As an example of the use of the Newton-Raphson method, let us consider the case of 2 materials. Equation (6) takes the form $$A(\lambda_{1a}) = \alpha_1 d_1 + g_1(\alpha_2)d_2$$

$$A(\lambda_{2a}) = f_1(\alpha_1)d_1 + g_2(\alpha_2)d_2$$

$$A(\lambda_{1b}) = f_2(\alpha_1)d_1 + \alpha_2 d_2$$

$$A(\lambda_{2b}) = f_3(\alpha_1)d_1 + g_3(\alpha_2)d_2 \quad (8)$$

The Newton-Raphson equations are;

$$A(\lambda_{1a}) - X_{1a} = \frac{\partial X_{1a}}{\partial \alpha_1}\Delta\alpha_1 + \frac{\partial X_{1a}}{\partial d_1}\Delta d_1 + \quad (9)$$

$$\frac{\partial X_{1a}}{\partial \alpha_2}\Delta\alpha_2 + \frac{\partial X_{1a}}{\partial d_2}\Delta d_2$$

$$A(\lambda_{2a}) - X_{2a} = \frac{\partial X_{2a}}{\partial \alpha_1}\Delta\alpha_1 + \frac{\partial X_{2a}}{\partial d_1}\Delta d_1 +$$

$$\frac{\partial X_{2a}}{\partial \alpha_2}\Delta\alpha_2 + \frac{\partial X_{2a}}{\partial d_2}\Delta d_2$$

$$A(\lambda_{1b}) - X_{1b} = \frac{\partial X_{1b}}{\partial \alpha_1}\Delta\alpha_1 + \frac{\partial X_{1b}}{\partial d_1}\Delta d_1 +$$

$$\frac{\partial X_{1b}}{\partial \alpha_2}\Delta\alpha_2 + \frac{\partial X_{1b}}{\partial d_2}\Delta d_2$$

$$A(\lambda_{2b}) - X_{2b} = \frac{\partial X_{2b}}{\partial \alpha_1}\Delta\alpha_1 + \frac{\partial X_{2b}}{\partial d_1}\Delta d_1 +$$

$$\frac{\partial X_{2b}}{\partial \alpha_2}\Delta\alpha_2 + \frac{\partial X_{2b}}{\partial d_2}\Delta d_2$$

In order to determine the characteristic wavelengths and extinction coefficients of a particular polymer film as a function of molecular orientation, and then the functional relationships among a group of extinction coefficients, it is necessary to monitor the behavior of the polymer film under applied stress. It has been empirically determined that the orientation behavior of blown films is adequately determined by uniaxially stretching a film of the polymer in the laboratory, and measuring the absorbance at each of the required wavelengths for a number of stretches. The absorbances are converted to absorption coefficients by dividing each absorbance by the thickness of the material after each stretch. The thickness is determined with a micrometer or optically by interferometric techniques. A series of such coefficients for each of the requisite number of wavelengths is thus obtained. Designating one series as the independent series, the functional dependence of each of the other series on the independent one is determined by the method of least squares. These functions are then used in the non-linear analysis described above in equation (6). When preparing the polymer for analysis, it is important that it not be recovered from solution, because the solvent usually interferes spectrally and because it causes the film to swell, yielding an incorrect film thickness. When using the method of interference fringes to determine the thickness of the films, it is important to measure fringe spacings in a region of little or no absorbance.

As an example, the stretch behavior of nylon 6, 6 in the machine direction was monitored for a series of eight stretches by a Perkin Elmer model 330 spectrophotometer. Nine spectra (8 stretches, plus initial) were measured at Brewster's angle, and the incident light was polarized in the machine direction, in order to eliminate interference fringes. A portion of the nylon macromolecule is pictured in FIG. 1. Four of the nine absorbance spectra are shown in FIG. 2. The others are omitted for the sake of clarity. It should be noted that the absorbances decrease as the film is stretched, since the film becomes thinner. However, not all absorbances decrease by the same amount. The largest absorption peak occurs at 2296 nm. This peak is chosen first because the detector is most sensitive to changes in thickness at this wavelength. Its reference wavelength is chosen at 2228 nm. because it shares a common baseline with the 2296 nm. absorption peak. Changes in the baseline will be the same at both wavelengths. Hence, baseline changes will cancel when the absorbance difference is taken. As is evident from FIG. 2, the largest difference in the change of absorption coefficients resulting from stretch occurs between $\alpha_{2296\text{-}2228}$ and $\alpha_{2050\text{-}1990}$.

The reference wavelength for the 2050 nm. absorption is chosen at 1990 nm. We find that, by dividing absorbance by thickness, the absorption coefficient $\alpha_{2050\text{-}1990}$ increases as the polymer is more completely oriented in the machine direction, while $\alpha_{2296\text{-}2228}$ decreases. In general, the two wavelengths used to characterize the thickness and orientation of a material should be chosen such that the absorption coefficients at these wavelengths each change more than 5% over the range of orientation. In addition, a graph of one vs. the other should have a slope of magnitude greater than 0.05. A slope of 0.0 would indicate that use of the dependent $\alpha$ is unnecessary, since it does not change with orientation. A graph of $\alpha_{2296\text{-}2228}$ versus $\alpha_{2050\text{-}1990}$ is shown in FIG. 3. Assuming a linear relationship between the two $\alpha$'s, least squares analysis gives the following:

$$\alpha_{2050\text{-}1990} = 0.0271 - 0.308\, \alpha_{2296\text{-}2228}.$$

This best-fit straight line is shown in FIG. 3. If orientation is not accounted for, i.e., if a constant value is assigned to the absorption coefficient, then there is a potential for thickness errors of about 25%.

Under uniaxial stress in the machine direction, nylon 6, 6 is predicted to orient with its carbon chain in a zig zag arrangement (FIG. 1a) in the machine direction; the plane defined by the zig zag is coincident with the plane of the film. Consequently, absorbances associated with nylon's various vibrational modes are predicted to occur in specific directions relative to the measurement axis system defined by the machine direction (x), transverse direction (y), and normal direction (z). Consider, for example, the fundamentals responsible for the absorptions at 2296 nm. and 2050 nm., respectively. These are pictured in FIG. 1, along with the associated directions of $d\vec{\mu}$. The absorption at 2296 nm. is due to the combination of the C—H symmetric stretch at 3407 nm (FIG. 1b), and the H—C—H bend at 6983 nm (FIG. 1c). The direction of $d\vec{\mu}$ in both cases is the y direction. Therefore, the absorption coefficient at 2296 nm should decrease, for incident light polarized in the machine direction, with increasing orientation. This occurs, as noted above. The absorption coefficient at 2050 nm. is due to the combination of the N—H stretch at 3030 nm. (FIG. 1d) and a vibrational node at 6419 nm. whose main components are C—N stretch and N—H in-plane (x-y) bend (FIG. 1e). The $d\vec{\mu}$ for N—H stretching is in the transverse direction while that for the 6494 nm. fundamental is in the (x) machine direction. FIG. 1f shows how the two fundamentals combine to give a $d\vec{\mu}$ whose largest component is in the (x) machine direction. Therefore, the absorption coefficient at 2050 nm. should increase with increased orientation for incident light polarized in the machine direction. This also occurs, as noted.

There are instances in which the absorption coefficient does not change with orientation. This happens, for example, when the dipole moment in question is oriented parallel to the direction of applied stress. In such cases, only one wavelength is required to determine the gauge of the material in question. Then, there will be $(2n-1)$ equations and unknowns in equation (7). In this case, it is impossible to determine the orientation behavior of the material.

When determining the functional dependence of $\alpha_i(\lambda_j)$ on $\alpha_i(\lambda_i)$, it is often useful to first establish whether the stress causes changes in dipole moment only within the plane normal to the direction of propagation of the incident radiation. This is true if $\alpha_i(\lambda_i)$ is unchanged under stress when unpolarized light is used. In this event $\alpha_i(\lambda_i)$ is effectively constant for the wavelength in equation and the above analysis is not required to determine $\alpha_i(\lambda_j)$. However, this simplified treatment yields no information about the orientation under stress of the material. Thus, even in this event it is worthwhile probing the material with linearly polarized light to determine if $\alpha_i(\lambda_i)$ changes at least in the direction of the electric vector of incident light. In the event that the applied stress causes changes in dipole moment parallel to the direction of incident radiation, such that the projection onto the plane of the sample also changes, $\alpha_i(\lambda_i)$ will change even for unpolarized incident radiation.

There is an alternate way to determine the functional dependence of $\alpha_i(\lambda_j)$ on $\alpha_i(\lambda_i)$. As stated above, 2n equations are required to solve for the system of 2n unknowns. However, this does not means that 2n wavelengths are required. A total of n wavelengths are sufficient if the behavior at each wavelength is measured for two different polarization states. Thus, changes in dichroism can be used to determine the orientation behavior of the material. This method is not preferred because it requires at least one high quality polarizer and the ability to sample two polarization states, which requires the use of two polarized beams or modulation of one polarized beam.

Solution of equation (7) provides thicknesses and absorption coefficients for each of the materials in a multilayer structure. In some applications it is desirable to determine the orientation of the materials, in addition to, or instead of, the thicknesses. Orientation of the macromolecules can be determined from the absorption coefficient, as follows. A functional relationship exists between the absorption coefficient and molecular orientation. This relationship may be established, for example, by independently determining orientation by means of x-ray diffraction measurements, and absorption coefficient by optical methods. Thus, a look-up table or graph may be used to determine the degree of orientation that corresponds to each value of the absorption coefficient. Additionally, other physical or chemical properties of the material, which depend on orientation, may also be related to the absorption coefficient. If these relationships are unique, the absorption coefficient may be used to determine these physical or chemical properties. As an example, the barrier properties of some polymers are a monotonic function of degree of orientation. (S. A. Jabarin, "Orientation Studies of Poly(Ethylene Terephthalate)". Polymer Engineering and Science, Vol. 24, No. 5 (1984), p. 381). In such a case, knowledge of the absorption coefficient will allow determination of barrier properties according to the above described look-up table approach.

It should be noted that the methods of determining thickness and/or orientation of multilayer polymer films can be applied to single layer films. Although nuclear gauging is the more common means of measuring the thickness of single layer films, orientation cannot be determined by nuclear methods. The invention then can be used to determine simultaneously, the thickness and orientation of single layer polymer films.

The infrared (IR) region of the electromagnetic spectrum can be divided into two parts; that which causes energy absorption associated with fundamental modes of molecular vibration (2.7–50 microns) called the mid IR, and that which initiates absorption associated with overtones and combinations of these fundamentals (1–2.7 microns), called the near IR. The intensity of absorptions due to fundamentals is 1 to 2 orders of magnitude greater than that associated with overtones and combinations. Additionally, while the mid IR region is associated with vibrations due to all the molecular nuclei, the near IR is associated almost exclusively with vibrations of groups containing hydrogen. The differences in absorption coefficients between these two regions limit usefulness of the mid IR in gauging films that are more than 0.002" thick because many of the absorptions at the characteristic wavelengths of the materials in the film are essentially infinite. This makes it impossible to detect the difference in thickness among materials greater than about 0.002" thick. The near IR region, on the other hand, is well suited to measure films from 0.001" to 0.040", since absorbances in this region are much smaller than in the mid IR, as mentioned. The mid IR region is preferred for the gauging of film less than 0.001" thick because of its much greater sensitivity. The presence, in the near IR, of combinations and overtone bands associated primarily with hydrogen-containing groups, results in many fewer absorption peaks than in the mid IR. While the mid IR contains more structural information, it is also more cluttered and therefore it is more difficult to interpret spectra in this region.

Another consideration in comparing the use of near IR and mid IR analysis is the difference in physical implementation. Near IR optical systems utilize standard lenses and polarizers, which are inexpensive and in common use. Mid IR optical systems require either all-reflective components, or more exotic transmissive materials for lenses and polarizers. The mid IR components are much more expensive. Furthermore, the photo-detectors used in mid IR applications are extremely sensitive to the temperature of the detector, the optics, and the structure of the instrument, whereas near IR photodetectors are not nearly as thermally sensitive. This factor, coupled with the greater light level available from near IR light sources, leads to improved signal-to-noise ratios in near IR instruments.

Figure 4:
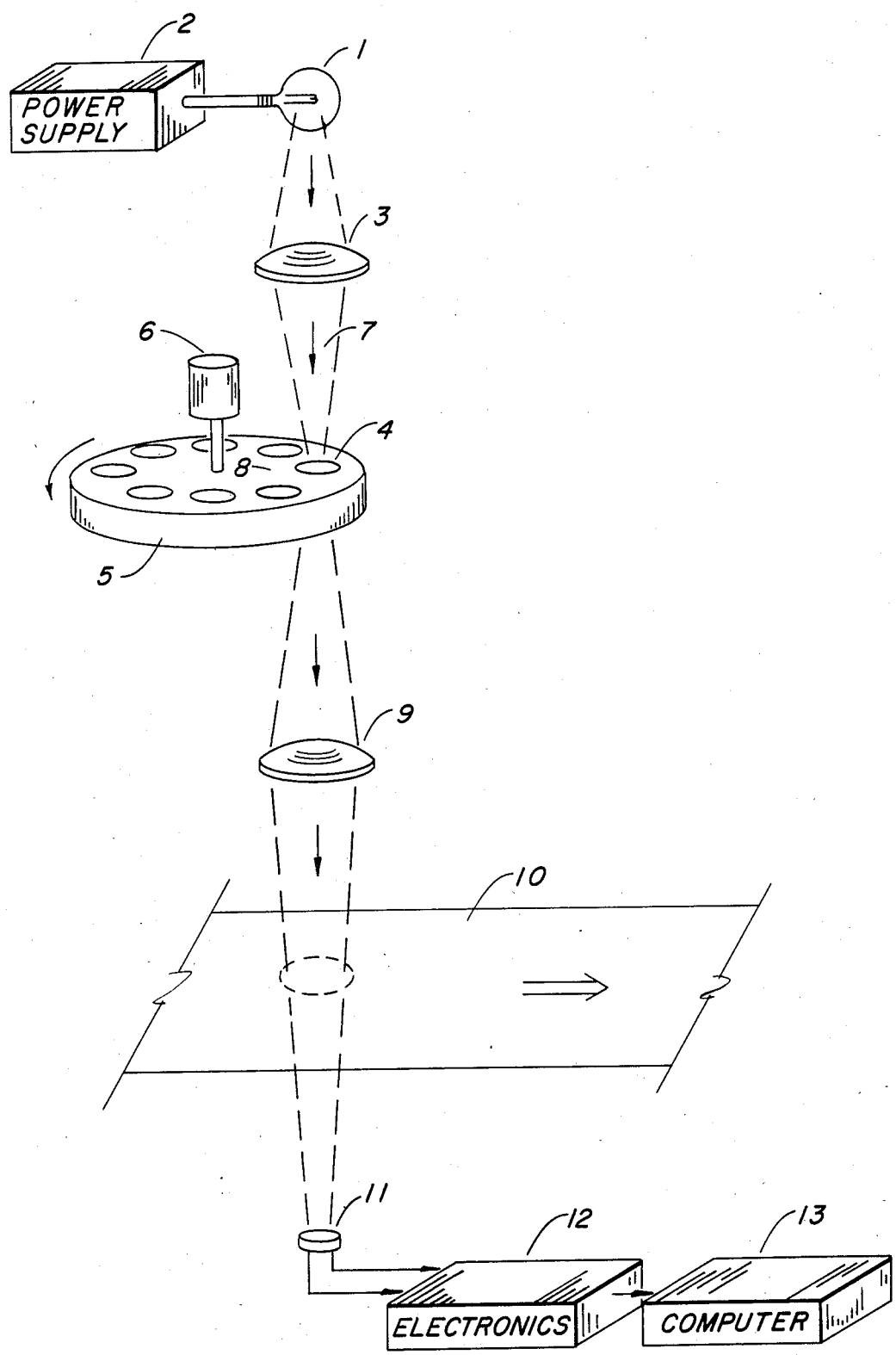
FIG. 4 is a block diagram of an optical system used to measure the transmittance of a sample.

FIG. 4 shows a block diagram of an optical system used to measure the transmittance of a sample. This is one possible embodiment of the invention. A light source 1 provides optical radiation over the full spectral range required by the instrument. For visible (0.4–0.7 microns) and near-infrared (0.7–2.7 microns) applications, a tungsten-filament lamp is usually used. A regulated power supply 2 provides a constant source of current to ensure a stable output from the light source 1. A collection lens 3 is used to gather light emitted by the source 1, and directs it through an optical filter 4 located in a rotating filter wheel 5. The filter 4 is used to isolate the band of wavelengths at which the transmittance measurement is to be made. The filter 4 is usually a multilayer interference filter, which can isolate a narrow band of wavelengths (e.g., less than 0.01 microns). The filter wheel 5 contains a number of such filters, in order to effect transmittance measurements at multiple wavelengths. The filter wheel 5 rotates at constant speed, driven by a motor 6. As each filter 4 moves into the beam of light 7 that is transmitted through the collection lens 3, it transmits its own narrow band of wavelengths. The intensity of light transmitted through each filter 4 increases as the filter moves into the beam 7, reaches a maximum when it is centered with respect to the beam, and then decreases as it moves out of the beam. The spaces 8 between filters 4 on the filter wheel 5 are larger than the diameter of the beam 7, so that the light transmitted past the filter wheel 5 is completely extinguished between filters 4. This allows various means of electronic correction for bias in the output, since the optical signal is truly equal to zero between filters.

Upon passing through each filter 4, the light is collected by a second lens 9, which projects it through the sample 10 to the photodetector 11. The sample 10 is shown as a portion of a moving web, as would be the case in a process measurement application. Off-line, laboratory measurements of small, stationary samples are equally possible. The photodetector 11 can be one of any number of photosensitive devices, including silicon, germanium, lead sulfide, lead selenide, indium antimonide, mercury-cadmium telluride, or a number of pyroelectric materials. The most common photodetector for the near-infrared region is lead sulfide. The electrical signals from the photodetector 11 are processed by the system electronics 12 for use by a computer 13. The computer 13 interprets the transmission measurements to calculate sample parameters such as the thicknesses and degrees of orientation of constituent materials.

Figure 5:
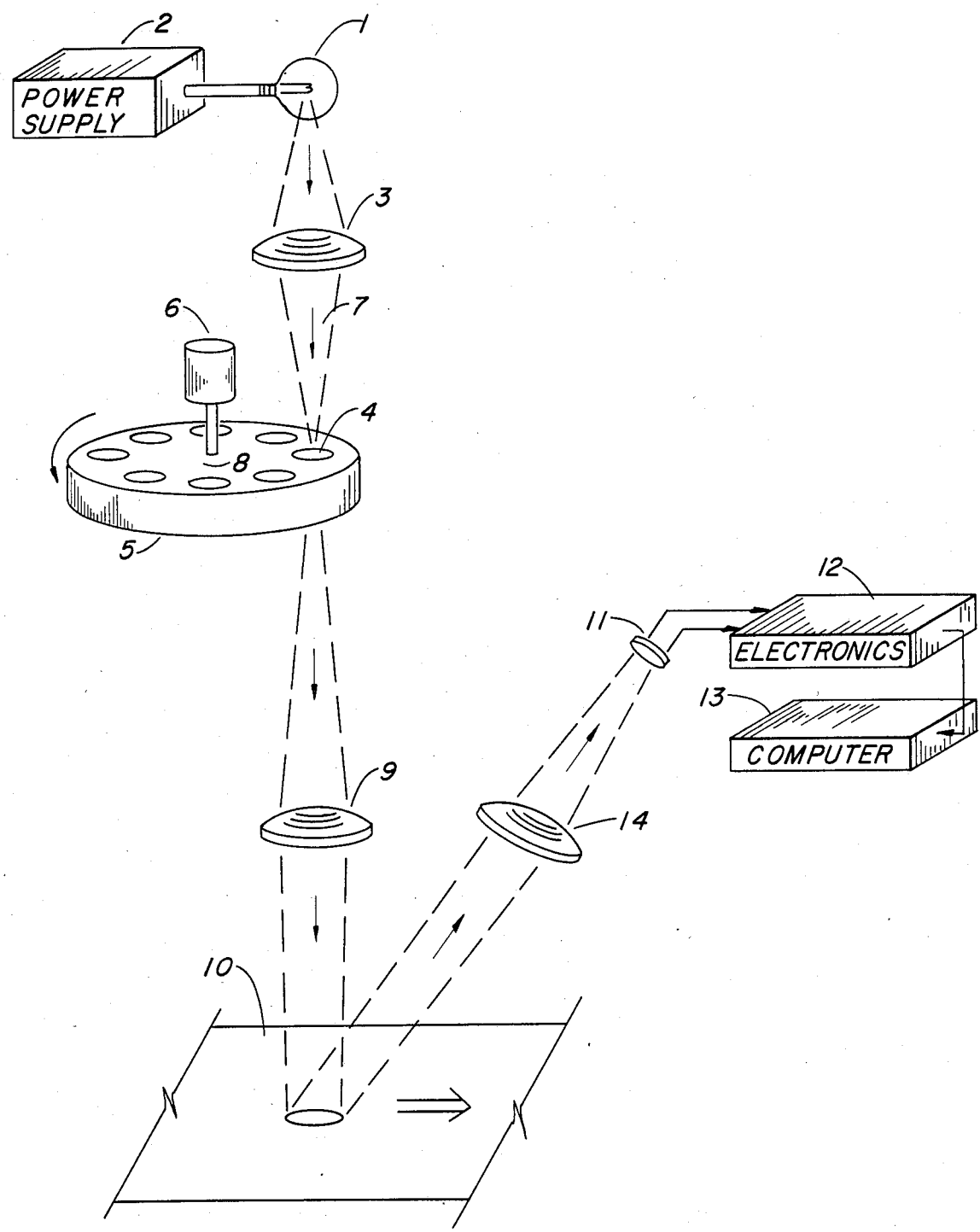
FIG. 5 is a block diagram of an optical system used to measure the reflectance of a sample.

A similar optical arrangement for measuring reflective samples is shown in FIG. 5. This configuration would be used for opaque or highly scattering samples, for which transmittance measurements are impractical, or for which a reflectance measurement provides more information. The system is similar to the transmittance system in FIG. 4, except that the light that passes through the second lens 9 is reflected from the sample 10, instead of being transmitted through it. An additional lens 14 is needed to collect the reflected light and direct it to the photodetector 11.

Figure 6:
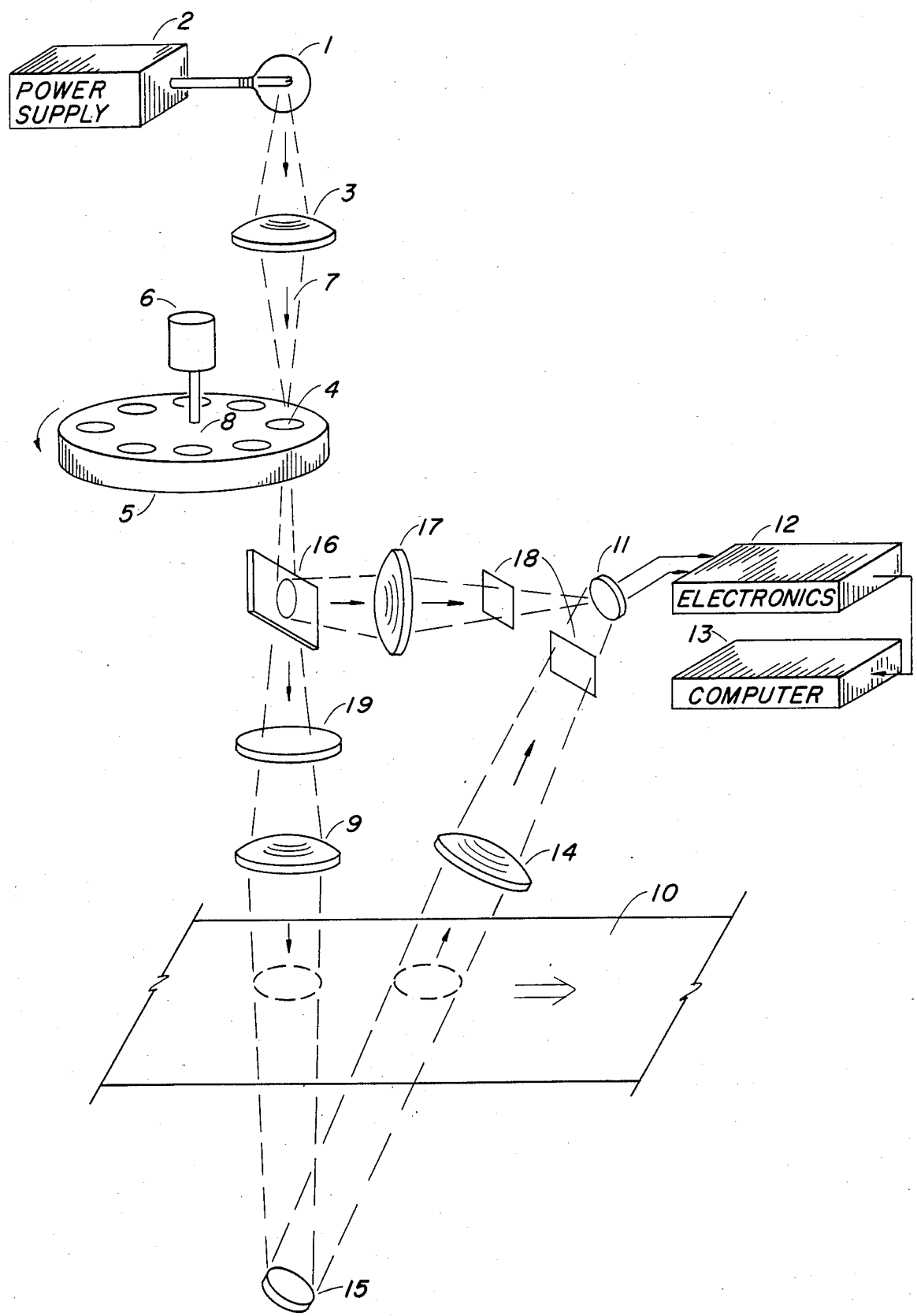
FIG. 6 is a block diagram of the preferred embodiment for measuring sample transmittance, utilizing a dual beam optical system.

The optical arrangement shown in FIG. 6 shares many of the features of the arrangement in FIGS. 4 and 5 with the notable addition of a reference path, which allows for dual beaming of the instrument, and a backing mirror 15, which allows for a second pass through the same sample 10. This second pass essentially doubles the path length through the sample 10 allowing for a more sensitive measurement.

Dual beaming greatly increases the stability and therefore the usefulness of the instrument. As in the arrangement of FIGS. 4 and 5, the measurement beam passes through lens 9 after emerging from the filter wheel 5 to the sample 10. The beam then passes through the sample 10 for the first time to a backing mirror 15. This mirror reflects the beam back through the sample 10 at an angle for a second pass. The beam is then collected by lens 14 and directed to detector 11. The reference path is created by a beam splitter 16. This beam splitter resides between the filter wheel 5 and lens 9 which directs the measurement beam to the sample 10. The function of the beam splitter 16 is to provide a reference beam which in reality is a sampling of the measurement before it is modified by the sample 10. The beam splitter consists of an optical substrate, with or without a coating, tilted at an angle with respect to the measurement beam. It typically reflects anywhere from 4% to 20% of the energy in the measurement beam. This reflected (reference) beam is directed by the lens 17 to detector 11. A shutter mechanism 18 resides between lenses 14 and 17 and the detector 11. It alternately blocks the reference beam or the measurement beam from detector 11, allowing the unblocked beam to hit the detector 11. This optical configuration allows the technique of dual beaming to be applied in on-line situations.

The reference path carries "information" about the measurement beam which is independent of the sample and therefore must be eliminated so that it does not interfere with the information in the measurement beam related to the sample.

An example of this misinformation would be any fluctuation in the intensity of the light source 1 due to a drift in power supply 2, changes in the efficiency of filter 4 and optical-mechanical movement. Each of these would change the measurement beam, falsely indicating a change in the sample 10. Typically, each movement signal is divided by or in some other manner ratioed by the reference signal. In this manner, the reference beam eliminates the false information from the measurement. Since both beams share a common detector, changes in the detector efficiency or electronic gain changes are negated. This technique allows for a stable, drift-free instrument. Because of the advantages of dual-beam operation, the embodiment shown in FIG. 6 is preferred.

For applications in which polarized light is required (for example, measurements of dichroism), a polarizing element is placed in either the illiminating or collecting optical systems. In FIG. 6, the polarizer 19 is shown immediately after the beamsplitter 16. A polarizing beamsplitter can be used to combine the functions of the beamsplitter 16 and polarizer 19.

As described above, the invention can be used to measure the thickness and degree of orientation of multilayer polymer films. Additionally, it is straightforward to use such measurements for control of the manufacturing process. In coextrusion, for example, thickness of the various polymers used in the structure can be independently controlled by varying extruder screw speeds. Degree of orientation can likewise be controlled by varying the diameter of the blown bubble (in blown film coextrusion), and by varying longitudinal stress applied by the take-up rollers. Although all layers are subjected to the same stress, the stress can be controlled so that all layers are at least adequately oriented for the application. If barrier properties have been adequately characterized as functions of orientation, then they can be controlled in the manufacturing process.

Figure 7:
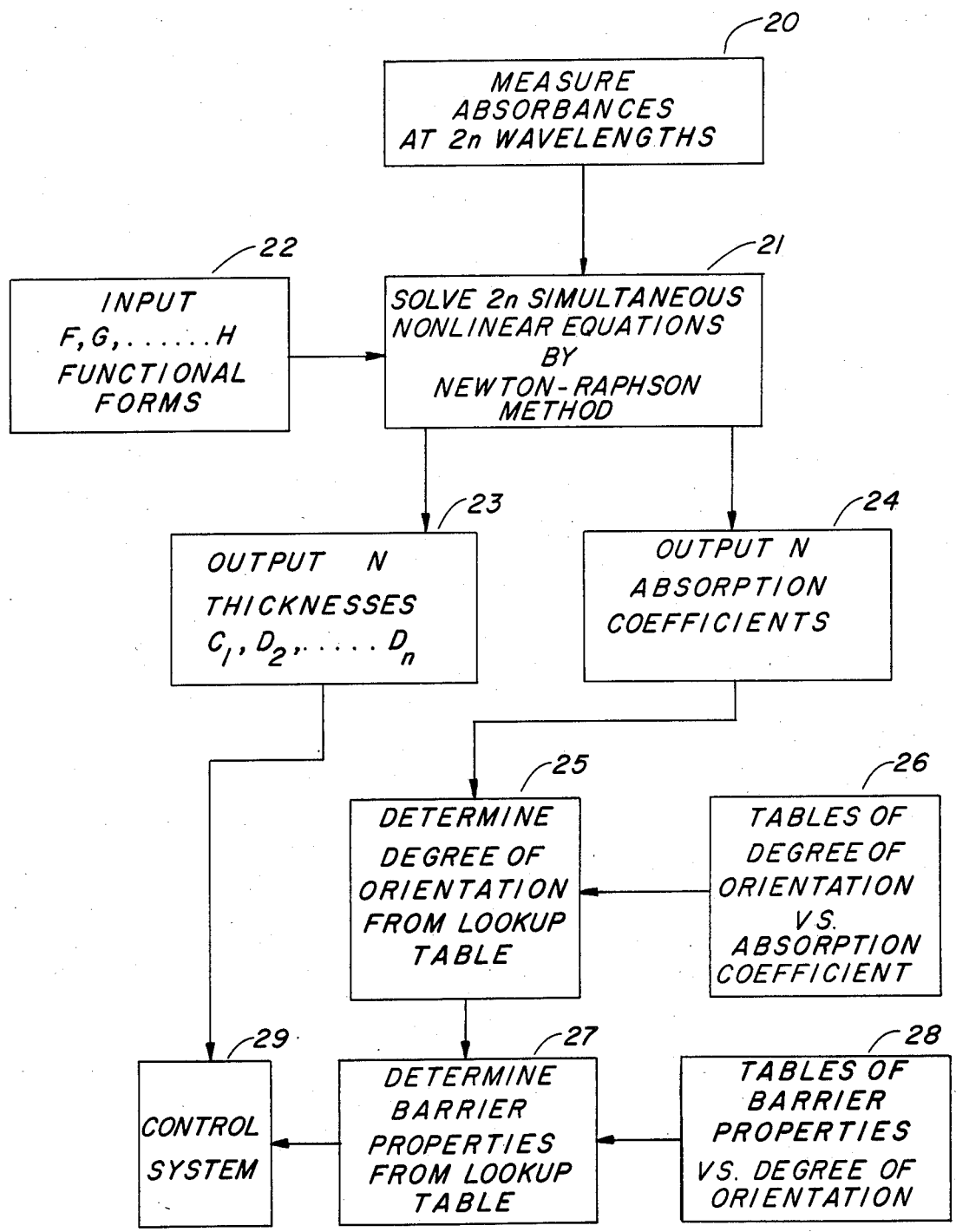
FIG. 7 is a flow chart showing how the invention can be applied to the measurement and control of a coextrusion process.

A flow diagram showing the steps by which the invention can be applied to measurement and control of a coextrusion manufacturing process is shown in FIG. 7. First, the coextruded sample is measured 20 at 2n wavelengths, where n is the number of materials in the coextrusion. The 2n absorbances comprise n pairs of wavelengths, one pair corresponding to each material. Each absorbance may be compensated for baseline variations by subtracting the absorbance at a nearby reference wavelength. (Some of the reference wavelength may be used in common for several of the 2n measurements). The 2n absorbances are then used to solve the 2n simultaneous nonlinear equations via the Newton-Raphson method 21. These are the equations set forth in equation (7). The solution of these equations require knowledge of the functional forms of the relationships between absorption coefficients (f, g, . . ., h) 22, which must be predetermined from a series of laboratory tests. The solution of the equations results in calculated thicknesses 23 and absorption coefficients 24. A table look-up approach can be used to determine degree of orientation from h the absorption coefficients 25, using tables 26 generated from laboratory experiments. Furthermore, barrier properties can likewise be determined 27 from tables 28 generated from laboratory measurements. It should be noted that tables 26 and 28 can be combined into a single table to allow determination of barrier properties directly from absorption coefficients. Once barrier properties are known, this information, in conjunction with the thickness, can be used to control 29 the coextrusion process, through control of, for example, extruder screw speeds, and take-up roller speed. It should also be noted that absorption coefficients can be used directly, in conjunction with thicknesses, for control.

While the invention has been described in its preferred embodiments, it is to be understood that the words which have been used are words are description rather than limitation, and that changes may be made within the purview of the appended claims without departing from the true scope and spirit of the invention in its broader aspects.

We claim:

1. Method of determining, simultaneously, the thickness and absorption coefficients of each of the materials in a multilayer structure, comprising the steps of:

measuring the first optical absorbance of each material of said multilayer structure at two or more wavelengths; and analyzing said first optical absorbances to simultaneously determine the thicknesses and absorption coefficients of said materials and, from said absorption coefficients, determine the degree of orientation of each said material.

2. Method, as recited in claim 1 wherein said wavelengths comprise a pair of wavelengths for each material in which the absorption coefficients change as a function of material orientation, and a single wavelength for each material in which the absorption coefficient does not change as a function of material orientation.

3. Method, as recited in claim 2, wherein each said pair of wavelengths is chosen such that the absorption coefficients at said wavelengths each change by more than 5% over the range of orientation encountered in the application.

4. Method, as recited in claim 3, wherein the rate of change of one absorption coefficient with respect to the other absorption coefficient, over the range of orientation encountered in the application, has a magnitude greater than 0.05.

5. Method, as recited in claims 1, 2, 3, or 4, where in said wavelengths are in the range 1–50 microns, and said multi-layer structure is a coextrusion.

6. Method, as recited in claims 1, 2, 3, or 4, where in said wavelengths are in the range 1–2.7 microns, and said multilayer structure is a coextrusion.

7. Method, as recited in claim 1, further comprising the step of controlling the thickness and degree of orientation of each of said materials in a coextrusion.

8. Method, as recited in claim 2, further comprising the step of controlling the thickness and degree of orientation of each of said materials in a coextrusion.

9. Method, as recited in claim 5, further comprising the steps of measuring second optical absorbances of said multilayer structure at one or more reference wavelengths, and subtracting said second absorbances from said first absorbances in order to compensate for absorbance baseline variations.

10. Method, as recited in claim 6, further comprising the steps of measuring second optical absorbances of said multilayer structure at one or more reference wavelengths, and subtracting said second absorbances from said first absorbances in order to compensate for absorbance baseline variation.

11. Method, as recited in claim 1, wherein said wavelengths comprise a single wavelength for each material, and said optical absorbances are measured at two mutually orthogonal polarizations at each said wavelength.

12. Method, as recited in claim 11, wherein said wavelengths are in the range 1–2.7 microns, and said multilayer structure is a coextrusion.

13. Method, as recited in claim 5, further comprising the step of determining the barrier properties of said materials from said absorption coefficients.

14. Method, as recited in clam 6, further comprising the step of determining the barrier properties of said materials from said absorption coefficients.

15. Method, as recited in claim 12, further comprising the step of determining the barrier properties of said materials from said absorption coefficients.

16. Method of determining, simultaneously, the thickness and absorption coefficients of a single layer film, comprising the steps of:
   measuring the optical absorbance of said film at two or more wavelengths; and
   analyzing said absorbances to simultaneously determine the thickness and absorption coefficients of said film and, from said absorption coefficients, determine the degree of orientation of said film.

17. Method of measuring, simultaneously, the thickess and absorption coefficients of a single layer film, comprising the steps of:
   measuring the optical absorbances of said film at a single wavelength for two mutually perpendicular polarizations; and
   analyzing said absorbances to simultaneously determine thickness and absorption coefficients of said film.

18. Method according to claim 17 wherein the degree of orientation of said film is determined from said absorption coefficient.

19. Apparatus for determining, simultaneously, the thickness and absorption coefficients of each of the materials in a multilayer structure, comprising:
   means for measuring the first optical absorbance of each material at two or more wavelengths; and
   means for analyzing said first optical absorbances to simultaneously determine the thicknesses and absorption coefficients of said materials and, from said absorption coefficients, determine the degree of orientation of each said material.

20. Apparatus, as recited in claim 19, wherein said wavelengths comprise a pair of wavelengths for each material in which the absorption coefficients change as a function of material orientation, and a single wavelength for each material in which the absorption coefficient does not change as a function of material orientation.

21. Apparatus, as recited in claim 20, wherein said wavelengths are in the range 1–50 microns.

22. Apparatus, as recited in claim 20, wherein said wavelengths are in the range 1–2.7 microns, and said multilayer structure is a coextrusion.

23. Apparatus, as recited in claim 22, wherein said measuring means comprises a light source, a rotating filter wheel containing a plurality of optical filters having spectral bands centered at said wavelengths, a first optical system for collecting light from said source and passing a portion thereof sequentially through each of said optical filters as each intersects the optical axis of said first optical system, a second optical system for collecting the light passing sequentially through each of said optical filters and directing it through said coextrusion, a mirror for reflecting the light back through said coextrusion, a third optical system for collecting the light passing back through said coextrusion and projecting it to a detection plane, a photo detector located in said detection plane for converting the light to analog electrical signals, and electronic means for converting said analog electrical signals to digital electrical signals; and wherein said analyzing means includes a computer.

24. Apparatus, as recited in claim 22, wherein said measuring means comprises a light source, a rotating filter wheel containing a plurality of optical filters having spectral bands centered at said wavelengths, a first optical system for collecting light from said source and passing a portion thereof sequentially through each of said optical filters as each intersects the optical axis of said first optical system, a second optical system for collecting the light passing sequentially through each of said optical filters and directing it through said coextrusion to a detection plane, a photodetector located in said detection plane for converting the light to analog electrical signals and electronic means for converting said analog electrical signals to digital electrical signals; and wherein said analyzing means includes a computer.

25. Apparatus, as recited in claim 23, further comprising beamsplitting means for isolating a portion of the light passing sequentially through each of said optical filters, a fourth optical system for collecting said portion and directing it toward said photodetector, and shutter means for blocking light from either said third or fourth optical system from said photodetector; and wherein said computer normalizes all measurements of light passing through said third optical system by measurements of light made through said fourth optical system.

26. Apparatus, as recited in claims 21, 24 or 25, wherein said light source includes a tungsten lamp, and said photodetector includes a lead sulfide cell.

27. Apparatus, as recited in claims 21, 24 or 25, which further includes a polarizing element in the sample illumination optical system.

28. Apparatus, as recited in claims 23, 24, or 25, which further includes a polarizing element in the collection optical system.

* * * * *

UNITED STATES PATENT AND TRADEMARK OFFICE
CERTIFICATE OF CORRECTION

PATENT NO. : 4,631,408

DATED : December 23, 1986

INVENTOR(S) : Zelmanovic, et al

It is certified that error appears in the above-identified patent and that said Letters Patent is hereby corrected as shown below:

Column 17, line 1, "21" should read "23"

Column 17, line 6, "21" should read "23"

Signed and Sealed this

Thirty-first Day of March, 1987

Attest:

DONALD J. QUIGG

*Attesting Officer*  *Commissioner of Patents and Trademarks*